United States Patent [19]

Breuer et al.

[11] 4,099,001
[45] Jul. 4, 1978

[54] [[[IMIDAZOLIDINYL AMINO]CARBONYL]AMINO]ACETYL CEPHALOSPORIN DERIVATIVES

[75] Inventors: Hermann Breuer; Uwe D. Treuner, both of Regensburg, Fed. Rep. of Germany

[73] Assignee: E. R. Squibb & Sons, Inc., Princeton, N.J.

[21] Appl. No.: 777,873

[22] Filed: Mar. 15, 1977

[51] Int. Cl.² .................................................. C07D 501/36
[52] U.S. Cl. ............................................. 544/27; 544/21;
260/332.2 A; 548/319; 548/318; 560/32
[58] Field of Search .................... 544/19, 21, 26, 27, 544/30

[56] References Cited
U.S. PATENT DOCUMENTS

| | | | |
|---|---|---|---|
| 3,687,641 | 8/1972 | Holdrege | 260/243 C |
| 3,833,568 | 9/1974 | Dolfini et al. | 260/243 C |
| 3,954,802 | 5/1976 | Kocsis | 260/243 C |
| 4,028,354 | 6/1977 | Breuer et al. | 260/243 C |

*Primary Examiner*—Donald G. Daus
*Assistant Examiner*—David E. Wheeler
*Attorney, Agent, or Firm*—Lawrence S. Levinson; Merle J. Smith

[57] ABSTRACT

[[[Imidazolidinyl amino]carbonyl]amino]acetylcephalosporin derivatives having the formula

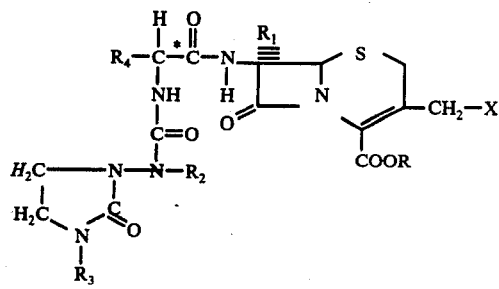

wherein R is hydrogen, lower alkyl, phenyl-lower alkyl, diphenyl-lower alkyl, tri(lower alkyl)silyl, trihaloethyl, a salt forming ion, or the group

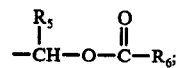

$R_1$ is hydrogen or methoxy; $R_2$, $R_3$ and $R_5$ each is hydrogen or lower alkyl; $R_4$ is hydrogen, lower alkyl, cyclo-lower alkyl, cyclo-lower alkenyl, cyclo-lower alkadienyl, phenyl, phenyl-lower alkyl, substituted phenyl, substituted phenyl-lower alkyl, or certain heterocyclic groups; $R_6$ is lower alkyl; and X is hydrogen, lower alkanoyloxy,

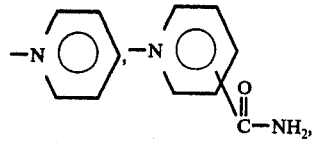

or certain heterothio groups; are useful as antibacterial agents.

11 Claims, No Drawings

[[[IMIDAZOLIDINYL AMINO]CARBONYL]AMINO]ACETYL CEPHALOSPORIN DERIVATIVES

BACKGROUND OF THE INVENTION

Cephalosporins having a ureido acyl side chain are disclosed in U.S. Pat. Nos. 3,673,183; 3,708,479, 3,833,568 and 3,860,591. Cephalosporins having various acyl side chains and a 7α-methoxy substituent are taught in various U.S. patents including U.S. Pat. Nos. 3,775,410; 3,780,031; 3,780,033; 3,780,034, 3,780,037; 3,843,641, etc.

Cephalosporins having an acylureido acyl side chain are disclosed in U.S. Pat. Nos. 3,687,949 and 3,925,368 and German Offenlegungsschrift Nos. 2,513,954 and 2,514,019. Our prior application Ser. No. 671,788, filed Mar. 30, 1976, discloses [[[(2,4-dioxo-1-imidazolidinyl-)amino]carbonyl]amino]acetyl cephalosporin derivatives.

SUMMARY OF THE INVENTION

It has now been found that new [imidazolidinyl amino]carbonyl]amino]acetylcephalosporin derivatives having the formula

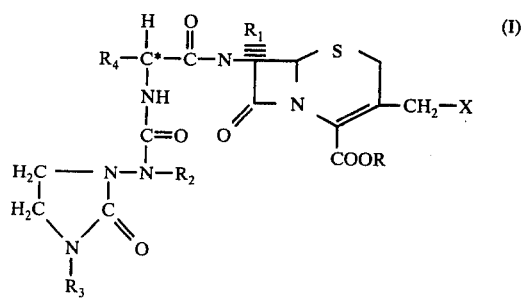

have useful antimicrobial activity.

R represents hydrogen, lower alkyl, phenyl-lower alkyl, diphenyl-lower alkyl, tri(lower alkyl)silyl, trihaloethyl, a salt forming ion, or the group $$-\overset{R_5}{\underset{|}{CH}}-O-\overset{O}{\underset{\|}{C}}-R_6$$

wherein $R_5$ is hydrogen or lower alkyl and $R_6$ is lower alkyl.

$R_1$ represents hydrogen or methoxy. The $R_1$ substituent is in the α-configuration as indicated by the broken lines ($\equiv$).

$R_2$ and $R_3$ each represents hydrogen or lower alkyl.

$R_4$ represents hydrogen, lower alkyl, cyclo-lower alkyl, cyclo-lower alkenyl, cyclo-lower alkadienyl, phenyl, phenyl-lower alkyl, substituted phenyl, substituted phenyl-lower alkyl, or certain heterocyclic groups.

X represents hydrogen, lower alkanoyloxy, certain heterothio groups,

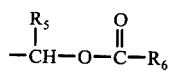, or 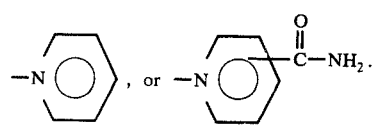

When X is pyridinium or carbamoyl substituted pyridinium, the compounds can be structurally represented as having the formula

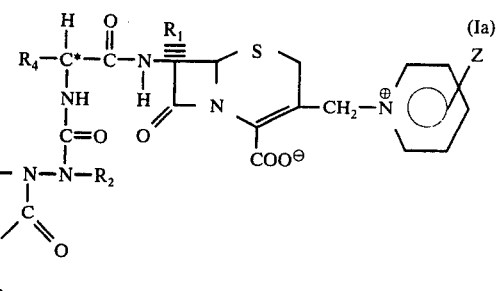

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons and especially 1 or 2 carbons. Examples of the type of groups contemplated are methyl, ethyl, propyl, isopropyl, butyl, t-butyl, etc. The lower alkoxy groups (referred to below) include such lower alkyl groups attached to an oxygen, e.g., methoxy, ethoxy, propoxy, etc. The phenyl-lower alkyl and diphenyl-lower alkyl groups include such lower alkyl groups attached to a phenyl with the same preferred groups as above but especially benzyl, phenethyl and diphenylmethyl.

The cyclo-lower alkyl groups are alicyclic groups having 3 to 7 carbons in the ring, i.e., cyclopropyl, cyclobutyl, cyclopentyl, cyclohexyl and cycloheptyl. The cyclolower alkenyl groups represent rings having 4 to 7 carbons with one double bond, i.e., cyclobutenyl, cyclopentenyl, cyclohexenyl, etc. The term cycloalkadienyl represents a ring having 6 or 7 carbons with two double bonds located at various positions such as 1,4-cyclohexadienyl which is especially preferred. The $C_5$-$C_6$ alicyclics are preferred.

The substituted phenyl and substituted phenyl-lower alkyl groups include those having one or two substituents on the phenyl ring, e.g., halogen (preferably chlorine or bromine), lower alkyl (preferably $C_1$-$C_4$ and especially methyl or ethyl), lower alkoxy (preferably $C_1$-$C_4$ and especially methoxy or ethoxy), or hydroxy, e.g., 2-, 3- or 4-chlorophenyl, 2-, 3- or 4-bromobenzyl, 2-, 3- or 4-hydroxyphenyl, 3,5-dichlorophenyl, 2-, 3- or 4-methylphenyl, 2-, 3- or 4-ethoxyphenyl, etc. The 4-monosubstituted phenyl groups are preferred.

The salt forming ions represented by R are metal ions, e.g., aluminum, alkali metal ions such as sodium or potassium, alkaline earth metal ions such as calcium or magnesium, or amine salt ions, of which a number are known for this purpose, for example, phenyl-lower alkylamines, such as dibenzylamine, N,N-dibenzylethylenediamine, lower alkylamines such as methylamine, ethylamine, tri(lower alkyl) amine such as triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)silyl group.

The heterocyclic groups represented by $R_4$ are 2-thienyl, 3-thienyl, 2-furyl, 3-furyl, 2-pyridyl, 3-pyridyl or 4-pyridyl. Also included within the meaning of $R_4$ are such heterocyclics having as a substituent $R_9$ which is halogen (preferably chlorine or bromine) or lower alkyl (preferably $C_1$-$C_4$ and especially methyl or ethyl) substituent, i.e., 2-(4-chlorothienyl), 3-(4-methylthienyl), etc.

The lower alkanoyloxy groups are the acyl groups of the lower fatty acids having the formula

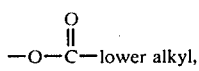

preferably wherein lower alkyl is of 1 to 4 carbons, especially methyl.

The heterothio groups represented by X are

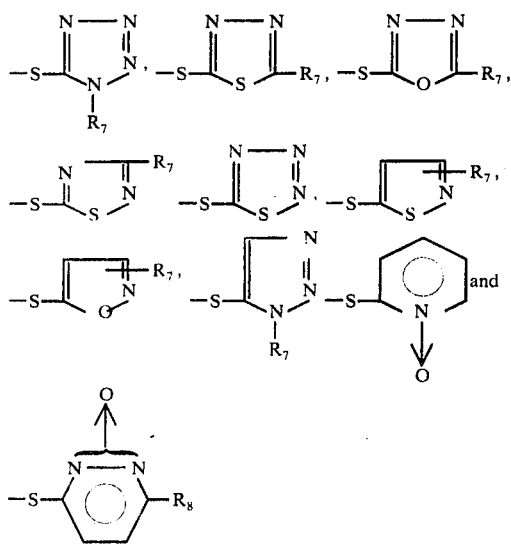

wherein $R_7$ is hydrogen or lower alkyl (preferably $C_1$-$C_4$ and especially methyl or ethyl) and $R_8$ is hydrogen, lower alkyl (preferably $C_1$-$C_4$ and especially methyl or ethyl), methoxy, hydroxy or halogen (preferably chlorine). Especially preferred are the tetrazole group above wherein $R_7$ is methyl, the 1,3,4-thiadiazole group above wherein $R_7$ is methyl and the 4-carbamylpyridinium group.

The compounds of formula I wherein $R_1$ is hydrogen can be prepared by several methods. For example, an α-amino intermediate of the formula

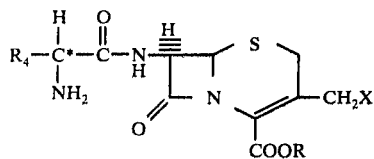

(II)

wherein X is hydrogen, lower alkanoyloxy, or heterothio can be reacted, preferably in the form of its trifluoroacetic acid salt, with an imidazolidine compound of the formula

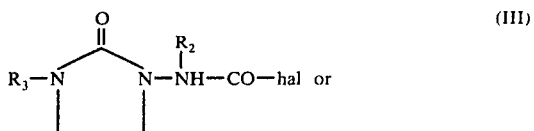

(III)

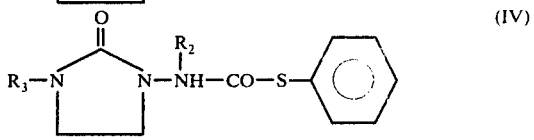

(IV)

wherein $R_2$ and $R_3$ are as defined above and hal is chlorine or bromine to yield the compound of formula I wherein $R_1$ is hydrogen and X is hydrogen, lower alkanoyloxy or heterothio.

The α-amino intermediate of formula II can be prepared by various methods such as by acylating a 7-amino cephalosporin of the formula

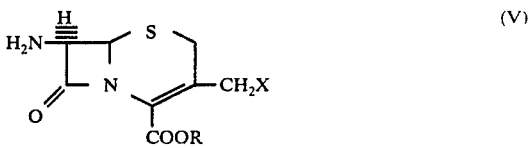

(V)

with a substituted α-amino acid of the formula

(VI)

wherein Y is a protecting group such as

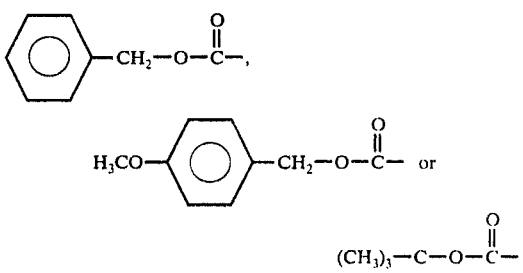

The α-amino protecting group is then removed by treating the resulting cephalosporin with trifluoroacetic acid and anisole. The α-amino compounds of formula II are taught in various U.S. patents as for example, U.S. Pat. Nos. 3,485,819; 3,507,861; 3,641,021; 3,796,801; 3,813,388; 3,821,207, etc.

Similarly, the 7α-methoxy compounds of formula I ($R_1$ is methoxy) wherein X is hydrogen, lower alkanoyloxy or heterothio can be prepared by reacting an α-amino intermediate of the formula

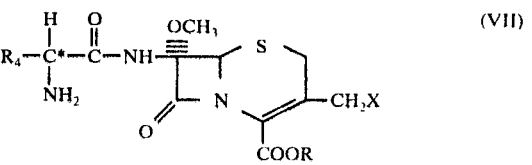

(VII)

preferably in the form of its trifluoroacetic acid salt with a compound of formula III or IV.

The 7α-methoxy intermediates of formula VII can be prepared in an analogous manner to the compound of formula II, i.e., by acylating a 7α-methyl-7β-aminocephalosporin of the formula

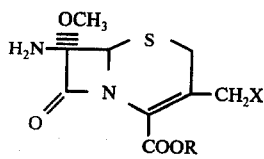

(VIII)

with a substituted α-amino acid of formula VI followed by removal of the protecting group. The compounds of formula VIII are taught in U.S Pat. No. 3,897,424 and the preparation of the compound of formula VII by various other methods are taught in U.S. Pat. Nos. 3,775,410; 3,780,031; 3,780,033; 3,780,034; 3,780,037; 3,887,549, etc.

The compounds of formula I wherein $R_1$ is either hydrogen or methoxy and X is pyridinium or carbamoyl substituted pyridinium are prepared by reacting the compound of the formula

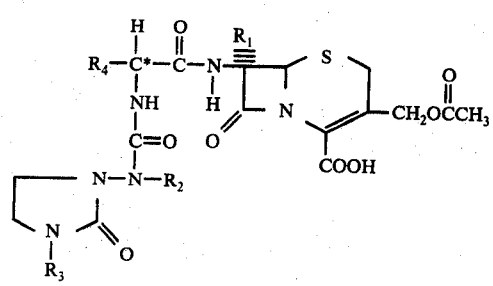

(Ib)

with pyridine or carbamoyl substituted pyridine (e.g., isonicotinamide) in a polar solvent such as water and in the presence of a catalyst such as an alkali metal thiocyanate. U.S. Pat. No. 3,792,047 and German Offenlegungsschrift No. 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ib with a mercaptan of the formula hetero—S—H    (IX)

or an alkali metal (preferably sodium) salt thereof of the formula hetero-S-alkali metal    (X)

Methods for displacing the acetoxy group of a cephalosporin by a heterothio group are taught in various U.S. Pat. including U.S. Pat. Nos. 3,855,213; 3,890,309; 3,892,737, etc.

The compounds of formula I wherein $R_3$ is hydrogen or lower alkyl and X is hydrogen, acetoxy or heterothio can also be prepared by reacting a compound of the formula

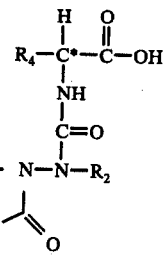

(XI)

or a derivative thereof wherein the hydroxy group is replaced with a known activating group, e.g., acid chloride, mixed anhydride, activated ester, etc., with an ester, e.g., trimethylsilyl or diphenylmethyl ester, of the compound of formula V or VIII, optionally in the presence of dicyclohexylcarbodiimide. The resulting ester is then treated according to methods known in the art, e.g., with water or with trifluoroacetic acid and anisole to yield the corresponding compound of formula I wherein R is hydrogen.

The preferred starting material of formula III is prepared from a 1-amino-2-imidazolidinone of the formula

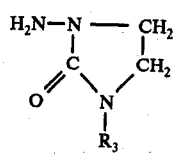

(XII)

which in turn is derived from a 2-imidazolidinone of the formula

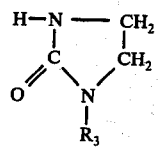

(XIII)

[utilizing the method described in J. Amer. Chem. Soc. 78, 5350 (1956)] as described in more detail in the examples.

The compounds of formula I wherein R is lower alkyl, phenyl-lower alkyl, trihaloethyl, diphenyl-lower alkyl or the acyloxymethyl group

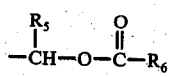

are obtained by reacting the 7-aminocephalosporin of formula V or VIII either before or after the acylation of the 7-aminosubstituent with one or two moles of a compound of the formula halo-R    (XIV)

or

    (XV)

wherein halo is preferably chlorine or bromine, in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e., R is hydrogen, with any of the salt forming ions described above.

Additional experimental details are found in the examples.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e., R is hydrogen, alkali metal, especially sodium or potassium, or diphenylmethyl); wherein X is hydrogen, lower alkanoyloxy, especially acetoxy, pyridinium, carbamoyl substituted pyridinium (particularly where the carbamoyl group is in the 4-position), 1-methyltetrazolylthio or 5-methyl-1,3,4-thiadiazolylthio; $R_1$ is hydrogen or methoxy, especially hydrogen; $R_4$ is cyclohexadienyl, phenyl, benzyl, phenethyl, substituted phenyl, benzyl or phenethyl wherein the substituent is on the phenyl ring and is one or two members selected from chloro, bromo, methyl, ethyl, methoxy, ethoxy and hydroxy or a substituted or unsubstituted heterocyclic selected from 2-thienyl,3-thienyl, 2-furyl,3-furyl,2-pyridyl,3-pyridyl and 4-pyridyl wherein the heterocyclic substituent is chloro,-bromo,methyl or ethyl; $R_2$ and $R_3$ each is hydrogen. When $R_3$ is other than hydrogen, methyl is preferred.

Compounds of formula I wherein X is

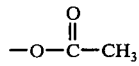

and $R_2$, $R_3$ and $R_4$ are as defined above are preferred as both final products and intermediates.

The most preferred final compounds are the acids and alkali metal salts of formula I wherein $R_4$ is 2-thienyl, 3-thienyl, phenyl or 4-hydroxyphenyl; and X is heterothio, particularly wherein X is

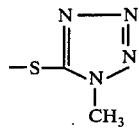

The compounds of formula I have a broad spectrum of antibacterial activity against both gram positive and gram negative organisms such as *Staphylococcus aureus, Salmonella schott muelleri, Pseudomonas aeruginosa, Proteus rettgeri, Escherichia coli, Enterobacter hafniae, Enterobacter cloacae, Klebsiella pneumoniae, Serratia mercescens*, etc. They may be used as antibacterial agents in a prophylactic manner or to combat infections due to organisms such as those named above, and in general may be utilized in a manner similar to cephalothin and other cephalosporins. For example, a compound of formula I or a physiologically acceptable salt thereof may be used in various mammalian species such as mice, rats, dogs, etc., in an amount of about 1 to 100 mg./kg., daily, orally or parenterally, in single or two to four divided doses to treat infections of bacterial origin, e.g., a dosage of 5.0 mg./kg. in mice.

About 10 to 400 mg. of an acid compound of formula I or a physiologically acceptable salt thereof can be incorporated in an oral dosage form such as tablet, capsule or elixir or in an injectable form in a sterile aqueous vehicle. The substance is compounded with a physiologically acceptable vehicle, excipient, binder, preservative, stabilizer, flavor, etc., in a unit dosage form as called for by accepted pharmaceutical practice. The amount of active substance in these compositions or preparations is such that a suitable dosage in the range indicated is provided.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

Injectable compositions are prepared by dissolving or suspending the active substance in a sterile vehicle such as water for injection or a natural vegetable oil such as sesame oil, cottonseed oil, peanut oil, soybean oil or the like or a synthetic fatty vehicle such as ethyl oleate. Antioxidants, buffers, preservatives and the like may also be included. The material can also be prepared in the dry form for reconstitution with such vehicles.

The following examples are illustrative of the invention and constitute especially preferred embodiments. They also serve as models for the preparation of other members of the group which can be produced by suitable substitution of starting materials. All temperatures are in degrees celsius.

EXAMPLE 1

(a)

D-2-[[[(4-Methoxyphenyl)methoxy]carbonyl]amino]-2-thiopheneacetic acid 74 g. of D-2-thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°–94°; $[\alpha]_{20}^{D}$: −69° (c = 1, tetrahydrofuran).

(b)

7β-Amino-3-[[(1-methyl-1H-tetrazolyl-5-yl)thio]methyl]-8-oxo-5-thia-1-azabicyclo[4.2.0]oct-2-ene-2-carboxylic acid To a stirred suspension of 27.2 g. of 7-amino cephalosporanic acid (0.1 mole) in 150 ml. of acetone and 100 ml. of water at 0°–5° is added 50 ml. of 2N sodium hydroxide, with care being taken to keep the pH below 8.5. A solution of 12.7 g. (0.11 mole) of 1-methyl-5-mercapto-1H-tetrazole in 50 ml. of 2N sodium hudroxide is added, and the mixture is allowed to warm to room temperature. The stirred mixture is then maintained at 60° (internal temperature) under nitrogen for 3 hours at pH 7–7.5 by the periodic addition of dilute aqueous sodium hydroxide. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

(c)

7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from part (b), 10.3 g. (0.054 mole) of p-toluenesulfonic acid monohydrate, 350 ml. of dioxane (dried by passage through basic alumina), and dry CH₃OH is stirred at room temperature under nitrogen for 30 minutes. The clear solution is evaporated to a residue, and water and CH₃OH are removed by four evaporations of 100 ml. quantities of dioxane. Fresh dioxane (300 ml.) is then added to the residue followed by a solution of crystalline diphenyldiazomethane (19.4 g., 0.01 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ in 250 ml. of water. The $CH_2Cl_2$ layer is washed with water and saturated NaCl, and finally dried (MgSO₄) to give a residue after removal of the solvent in vacuo. Treatment of the residue with Et₂O gives a solid (27 g.). Column chromatography of this solid on silica gel by elution with CHCl₃ and then EtOAc-CHCl₃ (4:1) provides the desired product as a residue (12.9 g.). Treatment with EtOAc then provides 8.0 g. of the desired product as a pale yellow powder.

(d)

7β-[[D-[[[(4-Methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 46.2 g. of 7β-3-[[(1-methyl-1H-tetrazol-5-yl)thio]methyl]-8-oxo-5-thia-1-azabicyclo[4.2.0]oct-2-ene-2-carboxylic acid, diphenylmethyl ester from part (c) are dissolved in 550 ml. of anhydrous methylene chloride, 550 ml. of tetrahydrofuran and 36 g. of D-2-[[[(4-methoxyphenyl)methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treated with activated carbon, filtered and the filtrate is then concentrated slowly under vacuum to a small volume. After standing overnight in the refrigerator, the precipitated crystals are filtered under suction to obtain 63.1 g. of 7β-[[D-[[[(4-methoxyphenyl)methoxy]carbonyl]amino]-2-thienylacetyl]amino]-3-[[(1-methyl-1H-tetrazol-5-yl)thio[methyl]-8-oxo-5-thia-1-azabicyclo[4.2.0]oct-2-ene-2-carboxylic acid, diphenylmethyl ester, m.p. 130°–131° (dec.). $[\alpha]_{20}^{D}$ −117° (c = 1, tetrahydrofuran).

(e)

7β-[D-2-Amino-2-(2-thienyl)acetamido]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt (1:1)

62 g. of the diphenylmethyl ester product from part (d) are added to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg and 35° bath temperature. The residue is treated with 250 ml. of petroleum ether, then 350 ml. of ether, stirred for 1 hour, and filtered with suction to yield 46.4 g. of 7β-[D-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1); m.p. 138°–139° (dec.).

EXAMPLE 2

(a)

L-2-[[[(4-Methoxyphenyl)methoxy]carbonyl]amino]-2-thiopheneacetic acid

L-2-Thienylglycine and p-methoxybenzyloxycarbonylazide are reacted according to the procedure of Example 1 (a) to yield L-2-[[[(4-methoxyphenyl)methoxy]carbonyl]amino]-2-thiopheneacetic acid; m.p. 97°–98°; $[\alpha]_{D}^{25}$ +68° (c = 1, tetrahydrofuran).

(b)

7β-[[L-[[[(4-Methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.-0]oct-2-ene-2-carboxylic acid, diphenylmethyl ester 4.6 g. of L-2-[[[(4-methoxyphenyl)methoxy]carbonyl]amino]-2-thiopheneacetic acid from part (a) and 5.9 g. of 7β-amino-3-[[(1-methyl-1H-tetrazol-5yl)thio]methyl]-8-oxo-5-thia-1-azabicyclo[4.2.0]oct-2-ene-2-carboxylic acid, diphenylmethyl ester from Example 1(c) are reacted according to the procedure of Example 1(d) to yield 8.4 g. of 7β-[[L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester which after concentration and treating with ether is obtained in amorphous form.

(c)
7β-[L-2-Amino-2-(2-thienyl)acetamido]-3-[[(-1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

1.6 g. of the diphenylmethyl ester product from part (b) are treated with trifluoroacetic acid and anisole according to the procedure of Example 1 (e) to yield 1.1 g. of 7β-[L-2-amino-2-(2-thienyl)acetamido]-3-[[(1-methyl-1H-tetrazol-5-yl)thio]methyl]-8-oxo-5-thia-1-azabicyclo[4.2.0]oct-2-ene carboxylic acid, trifluoroacetic acid salt (1:1); m.p. 127°-131° (dec.).

EXAMPLE 3

(a)
D-2-[[[(4-Methoxyphenyl)methoxy]carbonyl]amino]-phenyl acetic acid

D-2-phenylglycine and p-methoxybenzyloxycarbonylazide are reacted according to the procedure of Example 1 (a) to yield D-2-[[[(4-methoxyphenyl)methoxy]carbonyl]amino]phenylacetic acid.

(b)
7β-[[D-[[[(4-Methoxyphenyl)methoxy]carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 12 g. (0.025 mole) of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from Example 1 (c) and 7.7 g. (0.025 mole) of D-2-[[[(4-methoxyphenyl)methoxy]carbonyl]amino]phenylacetic acid from part (a) are reacted in the presence of 6.2 g. (0.025 mole) of dicyclohexylcarbodiimide according to the procedure of Example 1 (d) to yield 16 g. of light beige 7β-[[D-[[[4-methoxyphenyl)methoxy]carbonyl]amino]phenylacetyl]amino]-3-[[(1-methyl-1H-tetrazol-5-yl)thiomethyl]-8-oxo-5-thia-1-azabicyclo[4.2.0]oct-2-ene-2-carboxylic acid, diphenylmethyl ester, m.p. 147° (dec.)

(c)
7β-[D-2-Amino-2-phenylacetamido[-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

1.6 g. of the diphenylmethyl ester product from part (b) are treated with trifluoroacetic acid and anisole according to the procedure of Example 1 (e) to yield 10.1 g. of 7β-[D-2-amino-2-phenylacetamido]-3-[[(1-methyl-1H-tetrazol-5-yl)thio]methyl]-8-oxo-5-thia-1-azabicyclo[4.2.9]oct-2-ene-2-carboxylic acid, trifluoroacetic acid salt (1:1); m.p. 128°-130° (dec.).

EXAMPLE 4

(a)
7β-Methoxy-7β-[[DL-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.41 g. (0.0075 mole) of DL-2-[[[(4-methoxyphenyl)methoxy]carbonyl]amino]-2-thiopheneacetic acid (prepared according to the procedure of Example 1 (a) is dissolved in 50 ml. of dry methylene chloride, the solution is cooled in an ice bath to 0°-5°, and 0.969 g. (0.0075 mole) of diisopropylethylamine and isobutylchloroformate are added to the cold solution. After 10 minutes, 3.28 g. (0.00625 mole) of 7β-amino-7α-methoxy-3-[[(1-methyl-1H-tetrazol-5-yl)thio]methyl[-8-oxo-5-thia-1-azabicyclo[4.2.0]oct-2-ene-2-carboxylic acid, diphenylmethyl ester is added to the reaction mixture and the ice bath is removed. Following 3 hours of stirring at room temperature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatographed on silica gel (200 g., 60-200 mesh) and the desired product is eluted with 9:1 and 4:1 methylene chloride: ethyl acetate. The oily product is precipitated as a powder from a methylene chloride-ether mixture and dried over phosphorus pentoxide in vacuo to yield 3.81 g. of 7α-methoxy-7β-[[DL-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester.

Alternatively, the same compound can be obtained by the following procedure:

129 mg. (0.4 mmole) of DL-2-[[[(4-methoxyphenyl)methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirred solution of 77 mg. (0.147 mmole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 1 ml. of methylene chloride. After stirring at room temperature for 19 hours, the mixture is diluted with methylene chloride, washed with ph 7.4 buffer, and dried over sodium sulfate. Removal of solvent under reduced pressure yields a crude oil which is chromatographed on preparative thin layer chromatography silica gel plates developed in a 4:1 chloroform:ethyl acetate mixture. The desired product (58 mg.) is isolated as an oil.

(b)
7α-Methoxy-7β-[DL-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt The diphenylmethyl ester product from part (a) is reacted with trifluoroacetic acid in the presence of anisole according to the procedure of Example 1 (e) to yield 7α-methoxy-7β-[DL-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt.

EXAMPLE 5

1-[(Phenylmethylene)amino]-2-imidazolidinone 63 g. (0.73 mol.) of 2-imidazolidinone are dissolved in 2 liters of 2N sulfuric acid, the solution is cooled to 3°–6° and 50.5 g. (0.73 mol.) of sodium nitrite are added in small amounts over a period of 15 minutes. The solution is stirred for 1½ hours at 3°–6°. 110 g. (1.68 mol.) of zinc dust are added in small amounts over a period of 1 hour so that the temperature does not rise above 20°. At first the zinc dust goes quickly and completely into solution. The mixture is stirred for 30 minutes at 3°–6° and 60 minutes at room temperature. The undissolved zinc is filtered off and 70 g. (0.66 mol.) of benzaldehyde in 700 ml. of ethanol are added to the filtrate. After about 5 minutes, 1-[(phenylmethylene)amino]-2-imidazolidinone begins to crystallize. The mixture is stirred overnight at 5°–10°, then filtered under suction. The product is recrystallized from ethanol, yield 79.3 g.; m.p. 201°–206°.

EXAMPLE 6

1-Amino-2-imidazolidinone

A mixture of 120 ml. of concentrated hydrochloric acid and 120 ml. of water are heated to boiling. 15 g. of 1-[(phenylmethylene)amino]-2-imidazolidinone are added and the benzaldehyde which forms is rapidly distilled off. After 30 minutes, the distillation is discontinued and the clear solution is evaporated to dryness. The solid residue is triturated with ethanol to obtain 1-amino-2-imidazolidinone hydrochloride, yield 9.2 g.; m.p. 175°–179° (dec.).

The free base is obtained by admixing 8.8 g. of the hydrochloride with 185 ml. of methanol and 32 ml. of sodium methylate solution and refluxing the mixture for 15 minutes. It is filtered while hot and the filtrate is evaporated to dryness. The residue, 1-amino-2-imidazolidinone, crystallizes on trituration with ether. After dissolving with ethanol, filtering, concentrating and triturating with petroleum ether several times, 6.9 g. of product are obtained, m.p. 65°–69°.

EXAMPLE 7

1-(Chlorocarbonylamino)-2-oxoimidazolidine 1.01 g. (0.01 mol.) of 1-amino-2-imidazolidinone are dissolved in 20 ml. of anhydrous tetrahydrofuran and 20 ml. of a 1M solution of phosgene in toluene are added at 0°. The solution is stirred overnight at room temperature. The almost clear solution is filtered and evaporated to dryness. The 1-(chlorocarbonylamino)-2-oxoimidazolidine is obtained as an oily residue which is used without further purification.

EXAMPLE 8

3-[[(1-Methyl-1H-tetrazol-5-yl)thio]methyl]-8-oxo-7β-[[D-[[[(2-oxo-1-imidazolidinyl]amino]carbonyl]amino]-2-thienylacetyl]amino]-5-thia-1-azabicyclo[4.2.0]oct-2-ene-2-carboxylic acid 1.74 g. (0.003 mol.) of 7β-[D-[2-amino-2-thienylacetyl]amino]-3-[[(1-methyl-1H-tetrazol-5-yl)thio]methyl]-8-oxo -5-thia-1-azabicyclo[4.2.0]oct-2-ene-2-carboxylic acid, trifluoroacetic acid salt, are suspended in 24 ml. of acetonitrile and 3 ml. of bis(trimethylsilyl)acetamide are added. As soon as the solution becomes clear, there are added 6 ml. of 1,2-propylene oxide, and a solution of 0.005 mol. of 1-(chlorocarbonylamino)-2-oxoimidazolidine in anhydrous tetrahydrofuran. The mixture is stirred for 30 minutes at 0° then three hours at room temperature. 50 ml. of water are added, the mixture is stirred for 5 minutes and then extracted three times with ethyl acetate. The ethyl acetate extracts are washed with water, dried with magnesium sulfate and concentrated under vacuum. The residue is triturated with ether and filtered under suction to obtain 1.2 g. of 3-[[(1-methyl-1H-tetrazol-5-yl)thio]methyl]-8-oxo-7β-[[D-[[[(2-oxo-1-imidazolidinyl)amino]carbonyl]amino]-2-thienylacetyl]amino]-5-thia-1-azabicyclo[4.2.0]oct-2-ene-2-carboxylic acid, m.p. 180° (dec.).

The sodium salt is produced by bringing the acid obtained above its solution with an equivalent proportion of aqueous sodium bicarbonate solution and freeze drying the solution, m.p. 208°–215° (dec.).

EXAMPLE 9

(2-Oxo-1-imidazolidinyl)carbamothioic Acid, S-Phenyl Ester 3.2 ml. of (phenylthio)carbonyl chloride are dissolved in 30 ml. of dioxane and a solution of 2.63 g. of 1-amino-2-imidazolidinone in a mixture of 10 ml. of dioxane and 10 ml. of water is added. 2N sodium hydroxide solution is added dropwise at room temperature so that the pH is about 7.5–8.0. About 15 ml. of 2N sodium hydroxide are required. The dioxane is then distilled off. An oil separates which crystallizes after a short while to give 3.2 g. of (2-oxo-1-imidazolidinyl)carbamothioic acid, S-phenyl ester, m.p. 154°–159° (after recrystallization from ethyl acetate).

EXAMPLE 10

3-[[(1-Methyl-1H-tetrazol-5-yl)thio]methyl]-8-oxo-7β-[[D-[[[(2-oxo-1-imidazolidinyl]amino]carbonyl]amino]-2-thienylacetyl]amino]-5-thia-1-azabicyclo[4.2.0]oct-2-ene-2-carboxylic acid 1.16 g. (0.002 mol.) of 7β-[D-[2-amino-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt, and 0.82 ml. (0.006 mol.) of triethylamine are dissolved in 10 ml. of anhydrous dioxane and 0.55 g. (0.0023 mol.) of (2-oxo-1-imidazolidinyl) carbamothioic acid, S-phenyl ester are added. The solution is stirred for 6 hours at room temperature. Ether is then added and the triethylamine salt precipitates. This salt is dissolved in water, filtered and acidified with 2N hydrochloric acid. The precipitate, 3-[[(1-methyl-1H-tetrazol-5-yl)thio]methyl]-8-oxo-7β-[[D-[[[(2-oxo-1-imidazolidinyl)amino]carbonyl]amino]-2-thienylacetyl]amino]-5-thia-1-azabicyclo[4.2.0]oct-2-ene-2-carboxylic acid, is isolated, yield 1.0 g.

EXAMPLE 11

3-[(Acetyloxy)methyl]-7β-[[[[(2-oxo-1-imidazolidinyl)amino]carbonyl]amino]phenylacetyl]amino]-8-oxo-5-thia-1-azabicyclo[4.2.0]oct-2-ene-2-carboxylic acid By susbtituting 3-[(acetyloxy)methyl]-7β-[D-[2-amino-2-phenylacetyl]amino]-8-oxo-5-thia-1-azabicyclo[4.2.0]oct-2-ene-2-carboxylic acid, trifluoroacetic acid salt for the starting material in Example 8, 3-[(acetyloxy)methyl]-7β-[[[[(2-oxo-1-imidazolidinyl)amino]-8-5-thia-1-azabicyclo[4.2.0]oct-2-ene-2-carboxylic acid and its sodium salt are obtained.

EXAMPLE 12

3-[[4-(Aminocarbonyl)pyridinio]methyl]-8-oxo-7β-[[[[[(2-oxo-1-imidazolidinyl)amino]carbonyl]amino]phenylacetyl]amino]-5-thia-1-azabicyclo[4.2.0]oct-2-ene-2-carboxylic acid inner salt A mixture of 0.455 g. of 3-[(acetyloxy)methyl]-7β-[[[[[(2-oxo-1-imidazolidinyl)amino]carbonyl]amino]phenylacetyl]amino]-8-oxo-5-thia-1-azabicyclo[4.2.0]oct-2-ene-2-carboxylic acid, sodium salt, 0.146 g. of 4-pyridinecarboxamide, 1.92 g. of potassium thiocyanate and 1.2 ml. of water are heated at 50° for 24 hours. A chromatography column is filled with 30 g. of ion exchange resin (Amberlite XAD-2). 20 g. of a paste of the same ion exchange resin is admixed with the reaction mixture, stirred for 30 minutes and the mixture is poured into the column. The column is eluted with 750 ml. of water, then with a mixture of water and methanol (8:2). The eluate is collected in 10 ml. portions. Fractions 95–120 are concentrated and freeze dried to obtain 85 mg. of 3-[[4-(aminocarbonyl)pyridinio]methyl]-8-oxo-7β-[[[[(2-oxo-1-imidazolidinyl)amino]carbonyl]amino]phenylacetyl]amino]-5-thia-1-azabicyclo[4.2.0]oct-2-ene-2-carboxylic acid, inner salt.

EXAMPLE 13

7β-[[DL-[[[(2-oxo-1-imidazolidinyl)amino]carbonyl]amino]-2-thienylacetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid By substituting the 7α-methoxy-7β-[DL-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt of Example 4b in the procedure of Example 8, 7β-[[DL--[[[(2-oxo-1-imidazolidinyl)amino]carbonyl]amino]-2-thienylacetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid and its sodium salt are obtained.

EXAMPLE 14

(a)

3-[(Acetyloxy)methyl]-7α-methoxy-7β-[[DL-[[[(4-methoxyphenyl)methoxy]carbonyl]amino]-2-thienylacetyl]amino]-8-oxo-5-thia-1-azabicyclo[4.2.0]oct-2-ene-2-carboxylic acid, diphenylmethyl ester DL-2-[[[(4-methoxyphenyl)methoxy]carbonyl]amino]-2-thiopheneacetic acid and 3-[(acetyloxy)methyl]-7α-methoxy-7β-amino-8-oxo-5-thia-1-azabicyclo[4.2.0]oct-2-ene-2-carboxylic acid, diphenylmethyl ester are reacted according to the first procedure in Example 4 (a) to yield 3-[(acetyloxy)methyl]-7α-methoxy-7β-[[DL-[[[(4-methoxyphenyl)methoxy]carbonyl]amino]-2-thienylacetyl]amino]-8-oxo-5-thia-1-azabicyclo[4.2.0]oct-2-ene-2-carboxylic acid, diphenylmethyl ester.

(b)

3-[(Acetyloxy)methyl]-7α-methoxy-7β-[DL-2-amino-2-(2-thienyl)acetamido]-8-oxo-5-thia-1-azabicyclo[4.2.-0]oct-2-ene-2-carboxylic acid, trifluoroacetic acid salt (1:1)

The diphenylmethyl ester product from part (a) is reacted with trifluoroacetic acid in the presence of anisole according to the procedure of Example 1 (e) to yield 3-[(acetyloxy)methyl]-7α-methoxy-7β-[DL-2-amino-2-(2-thienyl)acetamido]-8-oxo-5-thia-1-azabicyclo[4.2.-0]oct-2-ene-2-carboxylic acid, trifluoroacetic acid salt (1:1).

(c)

3-[(Acetyloxy)methyl]-7α-methoxy-7β-[[DL-[[[(2-oxo-1-imidazolidinyl)amino]carbonyl]amino]-2-thienylacetyl]amino]-8-oxo-5-thia-1-azabicyclo[4.2.-0]oct-2-ene-2-carboxylic acid, sodium salt The trifluoroacetic acid salt product from part (b) is treated with the (2-oxo-1-imidazolidinyl)carbamothioic acid, s-phenyl ester from Example 9 according to the procedure of Example 10 to yield 3-[(acetyloxy)methyl]-7α-methoxy-7β-[[DL-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid.

An equimolar solution of this compound and sodium bicarbonate is lyophilized to yield 3-[(acetyloxy)methyl]-7α-methoxy-7β-[[DL-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid, sodium salt.

(d)

7α-Methoxy-7β-[[DL-[[[(2-oxo-1-imidazolidinyl)amino]carbonyl]amino]-2-thienylacetyl]amino]-3-[[4-(aminocarbonyl)pyridinio]methyl]-8-oxo-5-thia-1-azabicyclo[4.2.0]oct-2-ene-2-carboxylic acid An aqueous mixture of the sodium salt product of part (c), 4-pyridinecarboxamide, and potassium thiocyanate is reacted according to the procedure of Example 12 to yield 7α-methoxy-7β-[[DL-[[[(2-oxo-1-imidazolidinyl)amino]carbonyl]amino]-2-thienylacetyl]amino]-3-[[4-(aminocarbonyl)pyridinio]methyl]-8-oxo-5-thia-1-azabicyclo[4.2.0]oct-2-ene-2-carboxylic acid.

EXAMPLE 15

3-[(Acetyloxy)methyl]-7β-[[DL-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid By substituting 3-[(acetyloxymethyl]-7β-[[DL-[2-thienylacetylamino]-8-oxo-5-thia-1-azabicyclo[4.2.-0]oct-2-ene-2-carboxylic acid, trifluoroacetic acid salt for the starting material in Example 8, 3-[(acetyloxy)methyl]-7β-[[DL-[[[2-oxo-1-imidazolidinyl)amino]carbonyl]amino]-2-thienylacetyl]amino]-8-oxo-5-thia-1-azabicyclo[4.2.0]oct-2-ene-2-carboxylic acid and sodium salt are obtained.

EXAMPLE 16

7β-[[DL-[[[(2-oxo-1-imidazolidinyl)amino]carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid 0.003 mole of 3-[(acetyloxy)methyl]-7β-[[DL-[[[(2-oxo-1-imidazolidinyl)amino]carbonyl]amino]-2-thienylacetyl]amino]-8-oxo-5-thia-1-azabicyclo[4.2.-0]oct-2-ene-2-carboxylic acid, sodium salt from Example 15 and 0.004 mole of 2-mercaptopyridine, 1-oxide, sodium salt are dissolved in 15 ml. of water and heated overnight at 50°. The reaction mixture is then diluted with water, filtered, and the clear solution is adjusted to pH 2 by the addition of 2N hydrochloric acid. The resulting precipitate is filtered under suction to obtain 7β-[[DL-[[[(2-oxo-1-imidazolidinyl)amino]carbonyl]amino]-2-thienylacetyl]amino]-3-[[(1-oxo-2-pyridinyl)- thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid, sodium salt, there is obtained the corresponding final product in the L-form.

EXAMPLE 17

7β-[[D-[[[(2-oxo-1-imidazolidinyl)amino]carbonyl]amino-2-thienylacetyl]amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid, sodium salt is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[[D-[[[(2-oxo-1-imidazolidinyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid.

EXAMPLES 18–26

Following the procedure of Example 17 but substituting for the 1-oxopyridazine-3-thiol one of the following:

2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol there is obtained, respectively:

7β-[[D-[[[(2-oxo-1-imidazolidinyl)amino]carbonyl]amino]-2-thienylacetyl]amino]-3-[[(2-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-methyl-1-oxopyridazin-3yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-methoxy-1-oxopyridazin-3-yl]thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-t-butyl-2-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-ethyl-2-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-hydroxy-1-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-hydroxy-2-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-chloro-1-oxopyridazin-3-yl)thio]methyl]-8-oxo-5-thia-1-azabicyclo[4.2.0]oct-2-ene-2-carboxylic acid;

7β-[[D-[[[(2-oxo-1-imidazolidinyl)amino]carbonyl]amino]-2-thienylacetyl]amino]-3-[[(6-chloro-2-oxopyridazin-3-yl)thio]methyl]-8-oxo-5-thia-1-azabicyclo[4.2.0]oct-2-ene-2-carboxylic acid, respectively.

Similarly, by substituting 3-[(acetyloxy)methyl]-7α-methoxy-7β-[[D-[[[(2-oxo-1-imidazolidinyl)amino]carbonyl]amino-2-thienylacetyl]amino]-8-oxo-5-thia-1-azabicyclo[4.2.0]oct-2-ene-2-carboxylic acid, sodium salt for the 3-[(acetyloxy)methyl]-7β-[[D-[[[(2-oxo-1-imidazolidinyl)amino]carbonyl]amino]-2-thienylacetyl]amino-8-oxo-5-thia-1-azabicyclo[4.2.0]oct-2-ene-2-carboxylic acid, sodium salt in the foregoing procedure and utilizing each of the named thiols, the corresponding final products having a 7α-methoxy group are obtained.

The following additional compounds are produced by the procedure of Examples 7 and 8. The 1-amino-2-oxo-1-imidazolidine of formula A below, having the substituents $R_2$ and $R_3$ in the table, is converted to the chlorocarbonylamino derivative of formula B as in Example 7 then this intermediate is made to react with the intermediate of formula C below, having the substituents R, $R_4$ and X in the table, as in Example 8 to obtain the product of formula D, having the substituents in the table.

| A | B | C | | D | |
|---|---|---|---|---|---|
| Example | R$_2$ | R$_3$ | R$_4$ | R$_3$ R$_2$ | R | X |
| 27 | CH$_3$ | H | 2-thienyl | H CH$_3$ | t-C$_4$H$_9$ | -S-(5-methyl-1,3,4-thiadiazol-2-yl) |
| 28 | H | H | 2-thienyl | H H | -CH$_2$-C$_6$H$_{11}$ | -S-(1-methyl-1H-tetrazol-5-yl) |
| 29 | H | H | 4-methyl-2-thienyl | H H | -CH(C$_6$H$_{11}$)$_2$ | -S-(1-methyl-1H-tetrazol-5-yl) |
| 30 | H | H | 5-chloro-2-thienyl | H H | -CH$_2$CCl$_3$ | -S-(1-ethyl-1H-tetrazol-5-yl) |
| 31 | C$_2$H$_5$ | CH$_3$ | cyclohexyl | CH$_3$ C$_2$H$_5$ | -CH(C$_6$H$_5$)$_2$ | -S-(1-methyl-1H-tetrazol-5-yl) |
| 32 | H | C$_2$H$_5$ | 4-hydroxyphenyl | C$_2$H$_5$ H | -CH(C$_6$H$_5$)$_2$ | -S-(1-methyl-1H-tetrazol-5-yl) |
| 33 | H | H | phenyl | H H | H | H |
| 34 | H | t-C$_4$H$_9$ | 2-thienyl | t-C$_4$H$_9$ H | H | -S-(1-methyl-1H-tetrazol-5-yl) |
| 35 | CH$_3$ | CH$_3$ | 5-methyl-2-thienyl | CH$_3$ CH$_3$ | H | -O-CO-CH$_3$ |
| 36 | H | H | 5-methyl-2-furyl | H H | -C$_2$H$_5$ | -S-(1-methyl-1H-tetrazol-5-yl) |
| 37 | H | H | 2-furyl | H H | H | -S-(5-methyl-1,3,4-thiadiazol-2-yl) |
| 38 | H | H | 2-pyridyl | H H | t-C$_4$H$_9$ | -O-CO-C$_2$H$_5$ |

-continued

| | A | B | C | | | D | |
|---|---|---|---|---|---|---|---|
| Example | R$_2$ | R$_3$ | R$_4$ | R$_3$ | R$_2$ | R | X |
| 39 | H | H | 2-chloropyridin-5-yl | H | H | H | -S-tetrazolyl-N-CH$_3$ |
| 40 | H | H | pyridin-4-yl | H | H | H | -S-(1,3,4-oxadiazol-2-yl)-5-CH$_3$ |
| 41 | CH$_3$ | H | H | H | CH$_3$ | -(CH$_2$)$_2$-phenyl | -S-(1,3,4-thiadiazol-2-yl)-H |
| 42 | H | H | cyclopentyl | H | H | H | -S-(1,3,4-oxadiazol-2-yl) |
| 43 | H | H | -C$_2$H$_5$ | H | H | t-C$_4$H$_9$ | -O-CO-CH$_3$ |
| 44 | H | CH$_3$ | cyclohexyl | CH$_3$ | H | -CH(phenyl)$_2$ | -S-tetrazolyl-NH |
| 45 | H | H | phenyl | H | H | -CH(phenyl)$_2$ | -S-tetrazolyl-N-C$_2$H$_5$ |
| 46 | H | H | phenyl | H | H | H | H |
| 47 | H | H | phenyl | H | H | H | -S-tetrazolyl-N-CH$_3$ |
| 48 | H | H | phenyl | H | H | -CH$_2$-phenyl | -O-CO-CH$_3$ |
| 49 | C$_4$H$_9$ | H | phenyl | H | C$_4$H$_9$ | -CH(phenyl)$_2$ | -O-CO-CH$_3$ |
| 50 | H | H | phenyl | H | H | t-C$_4$H$_9$ | -S-tetrazolyl-N-CH$_3$ |
| 51 | H | H | -CH$_2$-phenyl | H | H | -CH(phenyl)$_2$ | -S-(1,3,4-thiadiazol-2-yl)-5-CH$_3$ |
| 52 | H | H | cyclohexenyl | H | H | -CH(phenyl)$_2$ | -S-(1,3,4-thiadiazol-2-yl)-5-CH$_3$ |

-continued

| | A | B | C | | | D | |
|---|---|---|---|---|---|---|---|
| Example | $R_2$ | $R_3$ | $R_4$ | $R_3$ | $R_2$ | R | X |
| 53 | $CH_3$ | H | cyclohexenyl | H | $CH_3$ | H | $-S-\text{(1-methyltetrazol-5-yl)}$ |
| 54 | H | H | 4-HO-phenyl | H | H | H | $-S-\text{(1-methyltetrazol-5-yl)}$ |
| 55 | H | $CH_3$ | 4-$CH_3$-phenyl | $CH_3$ | H | $-CH_2-CCl_3$ | $-S-\text{(5-methyl-1,3,4-oxadiazol-2-yl)}$ |
| 56 | H | H | 3,5-di-Cl-phenyl | H | H | $-CH(\text{C}_6\text{H}_5)_2$ | $-S-\text{(5-methyl-1,3,4-thiadiazol-2-yl)}$ |
| 57 | H | H | 4-$CH_3O$-benzyl | H | H | $t-C_4H_9$ | $-S-\text{(1-methyltetrazol-5-yl)}$ |
| 58 | H | H | 2-thienyl | H | H | H | $-S-\text{(4-methylthiazol-2-yl)}$ |
| 59 | H | H | phenyl | H | H | $-CH_2-\text{C}_6\text{H}_5$ | $-S-\text{(1,3,4-thiadiazol-2-yl)}$ |
| 60 | H | H | 2-thienyl | H | H | $-CH(\text{C}_6\text{H}_5)_2$ | $-S-\text{(4-methylthiazol-2-yl)}$ |
| 61 | H | H | 4-HO-phenyl | H | H | $-CH(\text{C}_6\text{H}_5)_2$ | $-S-\text{(4-methylisoxazol-5-yl)}$ |
| 62 | H | H | 2-thienyl | H | H | H | $-S-\text{(1H-tetrazol-5-yl)}$ |
| 63 | H | H | phenyl | H | H | H | $-S-\text{(1H-tetrazol-5-yl)}$ |
| 64 | H | H | 2-thienyl | H | H | Na | $-S-\text{(1,3,4-thiadiazol-2-yl)}$ |
| 65 | H | H | phenyl | H | $CH_3$ | $-CH_2-O-C(=O)-(t-C_4H_9)$ | $-S-\text{(1H-tetrazol-5-yl)}$ |

-continued

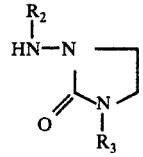

| Example | A R₂ | B R₃ | C R₄ | R₃ | R₂ | D R | X |
|---|---|---|---|---|---|---|---|
| 66 | H | H | (thienyl) | H | H | —CH₂—O—C(=O)—CH₃ | -S-(1-methyl-tetrazolyl) |
| 67 | H | H | (phenyl) | H | H | —CH₂—O—C(=O)—C₃H₇ | -S-(5-methyl-1,3,4-thiadiazolyl) |
| 68 | H | H | (thienyl) | H | H | —CH(CH₃)—O—C(=O)—CH₃ | -S-(1-methyl-tetrazolyl) |
| 69 | H | H | (phenyl) | H | H | —Si(CH₃)₃ | -S-(1-methyl-tetrazolyl) |

The following additional compounds are also produced by the procedure of Examples 7 and 8. The chlorocarbonyl derivative of formula E below (derived as in Example 7), having the substituents $R_2$, $R_3$ and $R_4$ in the table, is made to react with the 7-aminocephalosporanic acid derivative of formula F below as in Example 8 to obtain the product of formula G.

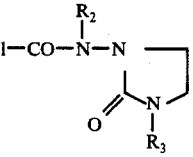

| Example | (E) R₂ | R₃ | (F) R₄ | R | (G) X |
|---|---|---|---|---|---|
| 70 | H | H | (thienyl) | t-C₄H₉ | -S-(5-methyl-1,3,4-thiadiazolyl) |
| 71 | H | H | (thienyl) | —CH₂—(phenyl) | -S-(1-methyl-tetrazolyl) |
| 72 | H | CH₃ | (thienyl) | H | -S-(1-methyl-tetrazolyl) |

-continued

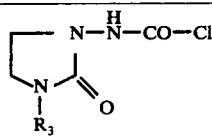 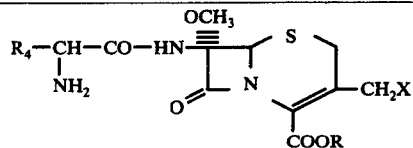 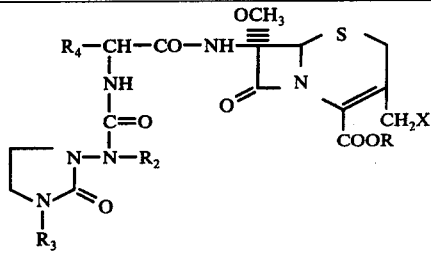

| | (E) | | (F) | | (G) |
|---|---|---|---|---|---|
| Example | $R_2$ | $R_3$ | $R_4$ | R | X |
| 73 | H | H | 2-chloro-thienyl | $-CH_2CCl_3$ | -S-tetrazole-N-$C_2H_5$ |
| 74 | H | H | 5-methyl-thienyl | $-CH(C_6H_5)_2$ | $-O-\overset{O}{\underset{\|}{C}}-CH_3$ |
| 75 | H | $C_2H_5$ | thienyl | $-CH(C_6H_5)_2$ | -S-tetrazole-N-$CH_3$ |
| 76 | H | H | thienyl | $t-C_4H_9$ | H |
| 77 | $C_2H_5$ | H | phenyl | $-CH(C_6H_5)_2$ | -S-tetrazole-N-$CH_3$ |
| 78 | H | H | 4-hydroxyphenyl | $-CH(C_6H_5)_2$ | -S-tetrazole-N-$CH_3$ |
| 79 | H | H | cyclohexyl | $-CH_2CCl_3$ | -S-tetrazole-N-$CH_3$ |
| 80 | H | H | cyclopentyl | $-CH(C_6H_5)_2$ | $-O-\overset{O}{\underset{\|}{C}}-CH_3$ |
| 81 | H | H | 5-methyl-furyl | $-C_2H_5$ | -S-tetrazole-N-H |
| 82 | H | H | furyl | H | -S-thiadiazole-$CH_3$ |
| 83 | H | H | pyridyl | $t-C_4H_9$ | $-O-\overset{O}{\underset{\|}{C}}-C_2H_5$ |
| 84 | H | H | 2-chloro-pyridyl | $-CH(C_6H_5)_2$ | -S-tetrazole-N-$CH_3$ |
| 85 | H | $CH_3$ | 4-pyridyl | K | -S-oxadiazole-$CH_3$ |

-continued

| | (E) | | (F) | | (G) |
|---|---|---|---|---|---|
| Example | R₂ | R₃ | R₄ | R | X |
| 86 | H | H | H | —(CH₂)₂—C₆H₅ | —S—(1,3,4-thiadiazol-2-yl)-H |
| 87 | H | H | —C₂H₅ | t-C₄H₉ | —O—CO—CH₃ |
| 88 | H | H | cyclohexyl | —CH(C₆H₅)₂ | —S—(1H-tetrazol-5-yl) |
| 89 | H | H | phenyl | —CH(C₆H₅)₂ | —S—(1-ethyl-tetrazol-5-yl) |
| 90 | H | H | phenyl | —CH(C₆H₅)₂ | —S—(1H-tetrazol-5-yl) |
| 91 | H | H | phenyl | —CH₂—C₆H₅ | —O—CO—CH₃ |
| 92 | H | H | phenyl | —CH(C₆H₅)₂ | |
| 93 | H | H | phenyl | —CH(C₆H₅)₂-H | H |
| 94 | H | H | phenyl | t-C₄H₉ | —S—(1H-tetrazol-5-yl) |
| 95 | CH₃ | H | C₆H₅—CH₂— | —CH(C₆H₅)₂ | —S—(5-methyl-1,3,4-thiadiazol-2-yl) |
| 96 | H | H | HO—C₆H₄— | —CH(C₆H₅)₂ | —S—(1-methyl-tetrazol-5-yl) |
| 97 | H | H | H₃C—C₆H₄— | —CH₂—CCl₃ | —S—(5-methyl-1,3,4-oxadiazol-2-yl) |
| 98 | H | H | 2,4-dichlorophenyl | —CH(C₆H₅)₂ | —S—(5-methyl-1,3,4-thiadiazol-2-yl) |
| 99 | H | H | H₃CO—C₆H₄—CH₂— | t-C₄H₉ | —S—(1-methyl-tetrazol-5-yl) |

-continued

| | (E) | | (F) | | (G) | |
|---|---|---|---|---|---|---|
| Example | $R_2$ | $R_3$ | $R_4$ | R | | X |
| 100 | H | H | 2-thienyl | $-CH(C_6H_5O)_2$ | | 2-methyl-1,3,4-thiadiazol-5-ylthio |
| 101 | H | H | phenyl | $-CH_2-C_6H_5$ | | 1,3,4-thiadiazol-2-ylthio |
| 102 | H | $CH_3$ | 2-thienyl | $-CH(C_6H_5O)_2$ | | 4-methylthiazol-2-ylthio |
| 103 | H | H | 4-hydroxyphenyl | H | | 5-methylisoxazol-3-ylthio |
| 104 | $CH_3$ | $CH_3$ | 2-thienyl | $-CH(C_6H_5O)_2$ | | 1H-1,2,3-triazol-4-ylthio |
| 105 | H | H | phenyl | H | | 1H-1,2,3-triazol-4-ylthio |
| 106 | H | H | 2-thienyl | $-CH_2-O-\overset{O}{\underset{\|}{C}}-CH_3$ | | 1-methyl-1,2,3-triazol-4-ylthio |
| 107 | H | H | phenyl | $-CH_2-O-\overset{O}{\underset{\|}{C}}-C_3H_7$ | | 2-methyl-1,3,4-thiadiazol-5-ylthio |
| 108 | H | H | 2-thienyl | $-CH(CH_3)-O-\overset{O}{\underset{\|}{C}}-CH_3$ | | 1-methyltetrazol-5-ylthio |
| 109 | H | H | phenyl | $Si(CH_3)_3$ | | 1-methyltetrazol-5-ylthio |

EXAMPLE 110

(a)
D-α-[[[(2-oxo-1-imidazolidinyl)amino]carbonyl]-amino]-2-thiopheneacetic acid 3.14 g. (0.02 mol.) of D-α-amino-2-thiophene acetic acid are suspended in 60 ml. of acetonitrile and 15.0 ml. of bis(trimethylsilyl)acetamide are added. The suspension is stirred until a clear solution of the trimethylsilyl ester results. 40.0 ml. of propylene oxide are added and then a solution of 3.55 g. (0.02 mol.) of 1-(chlorocarbonylamino)-2-oxoimidazolidine in 80 ml. of anhydrous acetonitrile is added dropwise, then stirred at room temperature overnight. The solvent is evaporated in vacuum, water is added to the oily residue, neutralized with sodium bicarbonate and again concentrated. The solid residue is triturated with ether and filtered under suction. After drying, 10 ml. of 2N hydrochloric acid is added to the residue. After a short time, D-α-[[[(2-oxo-1-imidazolidinyl)amino]carbonyl]amino]-2-thiopheneacetic acid crystallizes, which is purified by recrystallization from water.

(b) 3-[(Acetyloxy)methyl]-7β-[[D-[[[(2-oxo-1-imidazolidinyl)amino]carbonyl]amino]-2-thienylacetyl]amino]-8-oxo-5-thia-1-azabicyclo[4.2.0]oct-2-ene-2-carboxylic acid The product of part (a) is reacted with 7-amino cephalosporanic acid to obtain 3-[(acetyloxy)methyl]-7β-[D-[[[2-oxo-1-imidazolidinyl)amino]carbonyl]amino]-2-thienylacetyl]amino]-8-oxo-5-thia-1-azabicyclo[4.2.0]oct-2-ene-2-carboxylic acid.

What is claimed is:

1. A compound of the formula

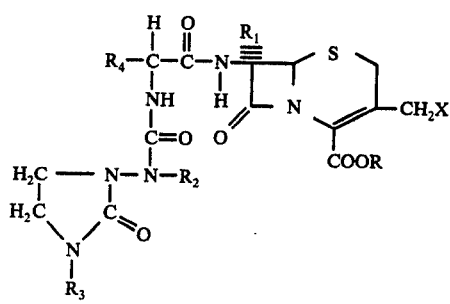

wherein R is hydrogen, lower alkyl, phenyl-lower alkyl, diphenyl-lower alkyl, tri(lower alkyl)silyl, trihaloethyl, aluminum, alkali metal, alkaline earth metal, phenyl-lower alkylamine, N,N-dibenzlethylenediamine, lower alkylamine, tri(lower alkyl amine), N-lower alkylpiperidine or

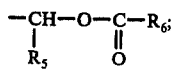

$R_1$ is in the α-configuration and is hydrogen or methoxy; $R_2$, $R_3$ and $R_5$ each is hydrogen or lower alkyl; $R_4$ is phenyl, phenyl-lower alkyl, substituted phenyl or phenyl-lower alkyl wherein said phenyl substituent is one or two members selected from the group consisting of halogen, lower alkyl, lower alkoxy and hydroxy, or a substituted or unsubstituted heterocyclic selected from the group consisting of 2-thienyl, 3-thienyl, 2-furyl and 3-furyl wherein said heterocyclic substituent is attached at an available carbon atom and is halogen or lower alkyl; $R_6$ is lower alkyl; and X is a heterothio group selected from the group consisting of

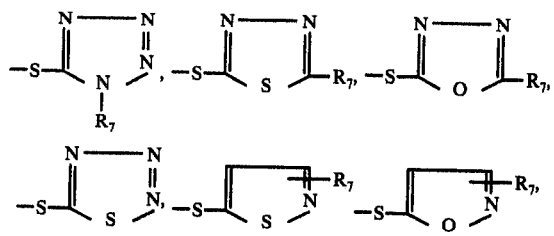

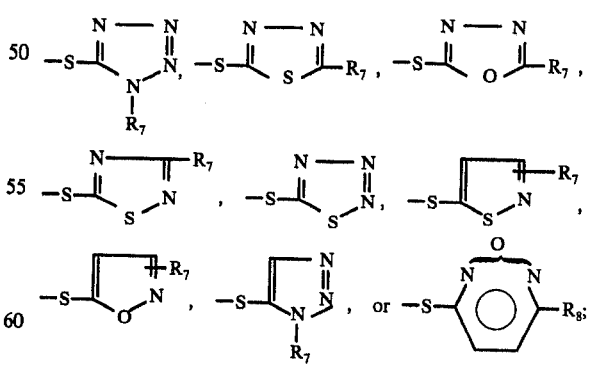

wherein $R_7$ is hydrogen or lower alkyl and $R_8$ is hydrogen, lower alkyl, methoxy, hydroxy or halogen.

2. A compound of claim 1 wherein R is hydrogen, alkali metal or diphenylmethyl; $R_1$ is hydrogen or methoxy; $R_2$ and $R_3$ each is hydrogen; $R_4$ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a substituted or unsubstituted heterocyclic selected from the group consisting of 2-thienyl, 3-thienyl, 2-furyl and 3-furyl wherein said heterocyclic substituent is attached at an available carbon atom and is chloro, bromo, methyl, or ethyl; and X is 1-methyltetrazolylthio of 5-methyl-1,3,4-thiadiazolylthio.

3. A compound of claim 1 wherein $R_4$ is phenyl.

4. A compound of claim 1 wherein $R_4$ is thienyl.

5. A compound of claim 1 wherein $R_2$ and $R_3$ each is hydrogen.

6. A compound of claim 1 wherein X is (1-methyl-1H-tetrazol-5-yl)thio.

7. The compound of claim 1 wherein $R_4$ is phenyl, R, $R_1$, $R_2$ and $R_3$ each is hydrogen and X is (1-methyl-1H-tetrazol-5-yl)thio.

8. The compound of claim 1 wherein $R_4$ is 2-thienyl; R, $R_1$, $R_2$ and $R_3$ each is hydrogen and X is (1-methyl-1H-tetrazol-5-yl)thio.

9. The compound of claim 1 wherein $R_4$ is phenyl, R is sodium, $R_1$, $R_2$ and $R_3$ each is hydrogen and X is (1-methyl-1H-tetrazol-5-yl)thio.

10. The compound of claim 1 wherein $R_4$ is 2-thienyl, R is sodium, $R_1$, $R_2$ and $R_3$ each is hydrogen and X is (1-methyl-1H-tetrazol-5-yl)thio.

11. A compound of claim 1 wherein X is $R_7$ and $R_8$ each is hydrogen or methyl.

UNITED STATES PATENT AND TRADEMARK OFFICE
CERTIFICATE OF CORRECTION

PATENT NO. : 4,099,001
DATED : July 4, 1978
INVENTOR(S) : Hermann Breuer et al.

It is certified that error appears in the above–identified patent and that said Letters Patent are hereby corrected as shown below:

Column 11, line 50, the beginning of the sentence should read
-- 16 g. of the -- .

Column 11, line 60, "7β" , first occurrence, should read -- 7α -- .

Column 13, line 25, insert a space between "A mixtureof" to read
-- A mixture of -- .

Signed and Sealed this

Twenty-sixth Day of June 1979

[SEAL]

Attest:

RUTH C. MASON
Attesting Officer

DONALD W. BANNER
Commissioner of Patents and Trademarks